United States Patent [19] [11] 4,019,519

Geerling [45] Apr. 26, 1977

[54] NERVE STIMULATING DEVICE

[75] Inventor: Leonardus Johannes Geerling, Hillsboro, Oreg.

[73] Assignee: Neuvex, Inc., Portland, Oreg.

[22] Filed: July 8, 1975

[21] Appl. No.: 594,024

[52] U.S. Cl. .......................................... 128/422

[51] Int. Cl.$^2$ .......................................... A61N 1/36

[58] Field of Search ............... 128/419 R, 421, 422, 128/423

[56] References Cited

UNITED STATES PATENTS

| | | | |
|---|---|---|---|
| 2,713,120 | 7/1955 | Mostofsky et al. | 128/423 |
| 3,503,403 | 3/1970 | Yarger | 128/421 |
| 3,521,641 | 7/1970 | Fargnsbach | 128/422 |
| 3,547,127 | 12/1970 | Anderson | 128/422 |
| 3,791,373 | 2/1974 | Winkler et al. | 128/422 |
| 3,902,502 | 9/1975 | Liss et al. | 128/422 |
| 3,908,669 | 9/1975 | Man et al. | 128/422 |
| 3,943,938 | 3/1976 | Wexler et al. | 128/421 |

FOREIGN PATENTS OR APPLICATIONS

| | | | |
|---|---|---|---|
| 866,375 | 4/1961 | United Kingdom | 128/422 |

*Primary Examiner*—William E. Kamm
*Attorney, Agent, or Firm*—Adrian J. LaRue

[57] ABSTRACT

A pulse generator for providing timed pulses of adjustable amplitude and constant width for nerve stimulation at selected portions of a body. The timed pulses of positive and negative amplitude are generated alternatinely and the period can be precisely set.

12 Claims, 2 Drawing Figures

18 OSC.
20 TRIGGER CIRCUIT
16 DRIVER CIRCUIT
10 POWER SUPPLY
12 DC TO DC CONVERTER CIRCUIT
14 SWITCHING CIRCUIT
ELEC.
ELEC.
22
23

NERVE STIMULATING DEVICE

BACKGROUND OF THE INVENTION

Nerve stimulation devices are available to be carried by a person and to apply electrical stimulation pulses to selected areas of the body. These conventional devices are bulky in size and weight for the reason that the batteries, which provide the required operating energy, are large. These batteries have to be replaced every few days which is burdensome and expensive, and they do not provide uniform operating duration. These stimulation devices also do not provide efficiently-generated stimulation pulses with adjustable amplitude.

In the case of a nerve stimulation device using single polarity nerve stimulation pulses, electrolysis takes place in a person's body because of effective DC component. This is true even if the stimulation pulses are fed through a capacitor or a transformer. In the case of dual polarity nerve stimulation pulses, the amplitude of the positive and negative pulses and width of the pulses must be equal, otherwise electrolysis will occur in the same manner as the single polarity nerve stimulation pulses.

SUMMARY OF THE INVENTION

This invention relates to a pulse generator circuit, and more particularly to a pulse generator circuit for providing timed pulses of adjustable amplitude and constant width for nerve stimulation at selected portions of a body.

An object of the present invention is to provide a pulse generator circuit that generates timed pulses of adjustable amplitude and constant width.

Another object of the present invention is the provision of a nerve stimulating device having a pulse generator circuit that generates timed pulses of adjustable amplitude and constant width.

A further object of the present invention is to provide an efficient DC and DC converter circuit including regulated positive and negative high voltage supplies through flyback and a low negative voltage supply through straight transformation during the conduction and flyback cycle to generate variable amplitude pulses of positive and negative polarity.

An additional object of the present invention is to provide a pulse generator circuit utilizing a low voltage power supply which generates a positive and negative power supply for operating CMOS circuitry.

Still a further object of the present invention is the provision of a low voltage power supply which generates low voltages for operating CMOS circuitry and high voltages for supplying switching transistors.

A still additional object of the present invention is to provide automatic shut off of discharge currents whenever any cell of a cell stack becomes discharged to avoid reverse charging of one cell by discharge of the other cells.

Still another object of the present invention is the provision of overvoltage protection circuit means to prevent the voltage from exceeding a maximum allowed output voltage.

Still an additional object of the present invention is to provide a circuit which generates pulses of predetermined pulse width including positive feed back for short rise and fall times to minimize battery drain during the transistion cycle in CMOS circuitry.

The forgoing and other objects of the present invention will become apparent when reference is made to the following description in conjunction with the accompanying drawing.

DETAILED DESCRIPTION OF THE INVENTION

Figure 1:
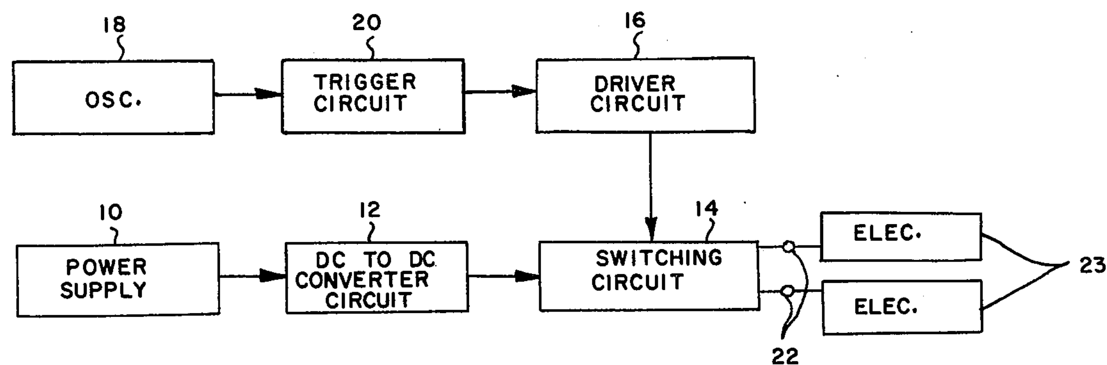
FIG. 1 is a block diagram of the pulse generator circuit.

Turning now to the drawing, FIG. 1 illustrates a block diagram of the pulse generator circuit which includes a power supply 10 comprising rechargeable batteries, a DC to DC converter circuit 12 connected to power supply 10 for converting low DC voltage to higher DC voltages, a switching circuit 14 connected to DC to DC converter circuit 12 and also driver circuit 16 is connected to switching circuit 14. An oscillator circuit 18 is connected to trigger circuit 20 which is turn is connected to driver circuit 16. Switching circuit 14 has an output terminal 22 which is connected to electrodes 23 secured a selected area of a body.

Figure 2:
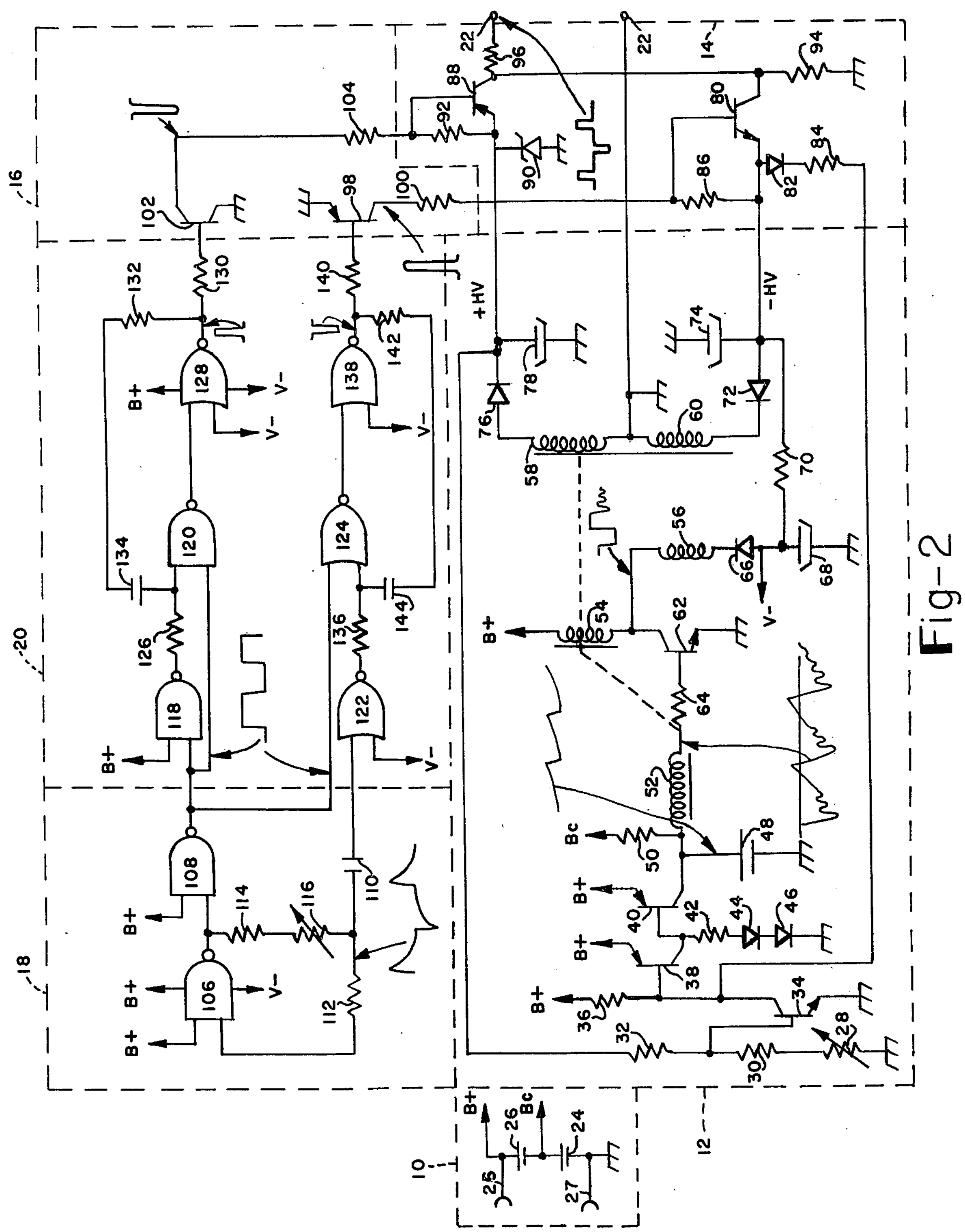
FIG. 2 is a schematic diagram of the pulse generator circuit of FIG. 1.

Turning now to FIG. 2, which is a schematic diagram of the block diagram of FIG. 1, power supply 10 includes series connected rechargeable batteries 24 and 26 connected between ground and $B^+$ whereas the connection between batteries 24 and 26 is connected to BC. Terminals 25 and 27 are provided for connection to a battery charging device as disclosed in U.S. Pat. application Ser. No. 508,200, filed Sept. 23, 1974.

The DC to DC converter circuit 12 has a potentiometer 28 connected between ground and series connected resistors 30 and 32. The base of transistor 34 is connected to resistors 30 and 32 while its emitter is connected to ground and its collector is connected to $B^+$ via resistor 36 and to the base of transistor 38. The emitter of transistor 38 is connected to $B^+$ while the collector is connected to the base of transistor 40 and to series connected resistor 42 and diodes 44 and 46 with diode 46 being connected to ground. The emitter of transistor 40 is connected to $B^+$ while the collector is connected to the junction of capacitor 48 and resistor 50 and to winding 52 of a transformer which also contains windings 54, 56, 58 and 60. Capacitor 48 is connected to ground and resistor 50 is connected to BC. The other side of winding 52 is connected to the base of transistor 62 via resistor 64. The emitter of transistor 62 is connected to ground while its collector is connected to the junction of windings 54 and 56. Winding 54 is connected to $B^+$ whereas winding 56 is connected to ground via a series connected diode 66 and capacitor 68. The junction of diode 66 and capacitor 68 is connected to V- and via resistor 70 to the junction of diode 72 and capacitor 74 which is connected to ground. Diode 72 is connected to series connected windings 58 and 60 with winding 58 being connected to diode 76. Resistor 32 is connected to the junction of diode 76 and capacitor 78 which is connected to ground. The outputs from windings 58 and 60 at the junctions of diode 72 and capacitor 74 and diode 76 and capacitor 78 respectively is negative high voltage −HV and positive high voltage +HV which are fed into switching circuit 14.

Switching circuit 14 includes a transistor 80 whose emitter is connected to the junction of diode 72 and capacitor 74 and to the collector of transistor 34 via series connected Zener diode 82 and resistor 84. The base of transistor 80 is connected to resistor 86 which is connected to the emitter of transistor 80. The emitter of transistor 88 is connected to the junction of diode 76 and capacitor 78, to ground via Zener diode 90 and to the base of transistor 88 via resistor 92. The collectors of transistors 80 and 88 are connected together to ground via resistor 94 and to one side of output 22 via resistor 96. The other side of output 22 is connected to the junction of windings 58 and 60 and it is grounded.

Driver circuit 16 includes transistor 98 whose collector is connected to the junction of resistor 86 and the base of transistor 80 via resistor 100 and whose emitter is connected to ground. Transistor 102 has its collector connected to the junction of resistor 92 and the base of transistor 88 via resistor 104 and its emitter is connected to ground.

Oscillator 18 includes logical Nand gates 106 and 108. One input to gates 106 and 108 is connected to $B^+$. The other input to gate 106 is a feedback circuit connected to the output of gate 108 and including series connected capacitor 110 and resistor 112. Gate 106 is also connected to $B^+$ and negative voltage—. The output from gate 106 is connected to gate 108 to provide the other input thereto. The output from gate 106 is also connected via series connected resistor 114 and potentiometer 116 to the junction of capacitor 110 and resistor 112.

Trigger circuit 20 includes gates 118 and 120 and NOR gates 122 and 124 which have one of their inputs connected to the output of Nand gate 108. The other input to gate 118 is connected to $B^+$. The output from gate 118 is connected to gate 120 via resistor 126 to provide the other input thereto. The output of gate 120 is connected as an input to inverter amplifier 128. The other input to amplifier 128 is connected to negative voltage V— and amplifier 128 is also connected to $B^+$ and negative voltage V—. The output of amplifier 128 is connected to the base of transistor 102 via resistor 130 and a feedback circuit including resistor 132 and capacitor 134 is connected between the output of amplifier 128 and the input to gate 120 that comes from the output of gate 118. The other input to NOR gate 122 is connected to negative voltage V— and the output from NOR gate 122 is connected via resistor 136 as an input to NOR gate 124. The output from NOR gate 124 is connected as an input to inverter amplifier 138 while the other input to amplifier 138 is connected to negative voltage V—. The output from amplifier 138 is connected to the base of transistor 98 via resistor 140. A feedback circuit which comprises a series connected resistor 142 and capacitor 144 is connected between the output of amplifier 138 and the input to NOR gate 124 coming from the output from NOR gate 122.

The operation of the pulse generator circuit is according to the following to provide timed pulses of adjustable amplitude and constant width preferably for nerve stimulation at selected areas of a body but such pulse generator circuit can be used for other purposes.

The DC to DC converter circuit 10 comprises a flyback system including switching transistor 62, the transformer, controllable current source transistor 40 with output control potentiometer 28, amplifier 38, sensing amplifier 34, buffer capacitors 74 and 78 and rechargeable batteries 24 and 26 in power supply 10. As long as the positive high voltage across the buffer capacitor 78 is below the adjusted value of potentiometer 28, the voltage at the base of transistor 34 will be too low to permit enough current to pass through the collector of transistor 34 and not enough voltage will be forced across resistor 36 to permit a base current in transistor 38, thus no collector current will occur through transistor 38. The current which is created by the voltage across the series network of resistor 42, diodes 44 and 46 and the base emitter junction of transistor 40 is permitted to slow into the base of transistor 40. The amplified current from the collector of transistor 40 charges capacitor 48 to its maximum rate. The voltage at the collector of transistor 40 now goes linearly positive from a negative voltage level. When the voltage passes a positive voltage level of about 0.5 volt, transistor 62 will become conductive and a voltage will be applied across winding 54 of the transformer. Due to transformer action, a voltage across winding 52 is generated and the polarity is such that the base voltage of transistor 62 is increased thereby causing transistor 62 to conduct more. This regenerative effect will drive the base of transistor 62 hard enough so that saturation is created whereby the battery voltage is connected across winding 54 and this will cause the current through winding 54 to increase linearly in value. The base current of transistor 62, which is set by the value of resistor 64, charges capacitor 48 in a reverse manner. The collector voltage of transistor 40 becomes more and more negative and at a certain moment the voltage value of capacitor 48 is such that the base current of transistor 62 is reduced and transistor 62 cannot maintain a saturated mode and the voltage of winding 54 will decrease in value causing the voltage in winding 52 to decrease and thus reducing the base current of transistor 62 even more. This will effectively collapse the magnetic field in the transformer and a flyback voltage will occur across all windings. A positive charge will be transmitted through diode 76 into buffer capacitor 78 and a negative charge will likewise be transmitted through diode 72 into buffer capacitor 74. The voltage across buffer capacitor 78 will increase positively and the voltage across buffer capacitor 74 will increase negatively.

As long as capacitor 78 is below the set value of potentiometer 28, a new cycle will start to charge capacitor 48 as many times as needed to bring the voltage at capacitor 78 to the set value of potentiometer 28. Because of the close coupling of windings 58 and 60, capacitors 74 and 78 will be charged up to the same voltage and the output voltage can be precisely set by potentiometer 28. When the voltage across capacitor 78 has reached the value corresponding to the value set by potentiometer 28, transistor 34 is turned on because the base voltage thereof has reached the value to permit base current to flow. Transistor 38 amplifies this current, and all the current, which previously was permitted to flow in the base of transistor 40, is shunted through transistor 38 and capacitor 48 is not permitted to charge to a positive value and capacitors 74 and 78 likewise are not permitted to charge. Resistor 70 is needed for equal discharge of capacitor 74 just as resistor 32 equally discharges capacitor 78. The small discharge current through resistor 70 is applied to capacitor 68 and negative voltage V— maximizes the efficiency of the circuit. Capacitor 68, which buffers the negative voltage V—, receives its charge from winding 56 via diode 66 during the conduction of transistor 62.

Resistor 50 guarantees a minimum charging current into capacitor 48 and, for this reason, the DC to DC conversion cycle is limited to a predetermined frequency to maintain a minimum charge at capacitor 68.

In case of malfunction in the sensing amplifier circuit, a runaway situation may occur, and the high voltage at capacitors 74 and 78 might increase to an undesirable high voltage level. To preclude this possible situation, a dual safety network is provided. The first safety circuit constitutes Zener diode 82 with a predetermined voltage and resistor 84 as a current limiter. When the voltage across capacitor 74 reaches the predetermined voltage level of Zener diode 82, Zener diode 82 starts conducting and turns transistor 38 on via resistor 84 which slows down or stops the operation of DC to DC converter circuit 12. In case of a failure in the current amplifier, current source circuitry and/or associated parts of the converter circuit, Zener diode 90 will clamp the output with its Zener voltage level.

Diodes 44 and 46 protect against reverse charging of the batteries during deep discharge of battery cells 24 and 26. When battery cells 24 and 26 become discharged and the voltage level reaches 1.5 volts or less, no current flow is possible into the base of transistor 38 and the converter circuit 12 goes to an idle state because the voltage drop across the emitter base of transistor 40 plus the voltage drop across diodes 44 and 46 will be equal to $B^+$ voltage. The idle mode will be discontinued when battery cell 26 becomes discharged less than 0.5 volt and the current through resistor 50 cannot bring transistor 62 into conduction.

As regards oscillator circuit 18, assume the operation thereof with the following starting points: Output of gate 108 at high voltage level, input of gate 108 at low voltage level and the input of gate 106 at high voltage level. The voltage across capacitor 110 is exponentially being charged with the negative current flowing through resistor 114 and potentiometer 116. The voltage level at both terminals of resistor 112 goes negative and when this voltage level passes the input threshold of gate 106, the output of gate 106 starts going positive and the output of gate 108 negative which drives the input even more negative via capacitor 110. This regenerates until the following conditions exist: input of gate 106 negative, output of gate 106 and input to gate 108 positive and the output of gate 108 negative. Now the input of gate 106 starts moving positive exponentially by charging capacitor 110 via resistor 114 and potentiometer 116, and, when the threshold of the input again is reached, the output of gate 106 starts moving negative. The gates 106 and 108 are CMOS devices which use extremely low current and most of the current drain occurs during the switching transistion cycle. During this switching transition, input of gate 106 is protected by resistor 112. The output of gate 108 is a symmetrical square wave and the period is controlled by the time value of potentiometer 116 constituting the pulse rate control and the period can be adjusted over a wide range. The unused inputs of gates 106 and 108 are connected to $B^+$ and the CMOS circuitry is powered by the battery voltage $B^+$ and negative voltage V−.

The CMOS trigger circuit 20 receives the output of oscillator 18 and produces a positive and negative trigger pulse of fixed pulse width and height with fast rise and fall times. The positive trigger pulses are produced by NAND gates 118 and 120 and inverter amplifier 128, the unused input of gate 118 is connected to positive voltage $B^+$. The negative trigger pulses are produced by NOR gates 122 and 124 and inverter amplifier 138, the unused inpus of gate 122 and amplifier 138 are connected to negative voltage V−. The positive trigger pulse occurs at the rising transition of the oscillator output and the negative trigger pulse occurs at the negative transition in accordance with the following: During the generation of the negative cycle of the oscillator output, the input therefrom to gates 118 and 120 is negative and the output of gate 118 which is the input to gate 120 is positive. The logical output of gate 120 is positive and the output of amplifier 128 is negative. At the instant the oscillator signal goes positive, the input of gate 118 and the output of gate 120 negative. The input from gate 118 to gate 120 is delayed by the propogation time of gate 118 and by the RC time constant of resistor 126 and capacitor 134 so the input to gate 120 from gate 118 stays at a logical positive level for the time determined by the RC network of resistor 26 and capacitor 134. When the input of gate 120 which receives the signal of gate 118 passes its input threshold, the output thereof goes to a logical positive value, which in turn provides a positive input to amplifier 128 and its output goes negative. The regenerative feedback via resistor 132 and capacitor 134 makes the transition time very short and this reduces the current drain through gate 120 and amplifier 128 substantially. For the same reason, the rise and fall times of the output trigger pulses are significantly shortened. The negative trigger pulses are generated in a similar manner via gates 122 and 124 and amplifier 138.

The operation of driver circuit 16 and switching circuit 14 is according to the following: Transistor 102 receives the positive trigger pulses from trigger circuit 20 and drives switching transistor 88 in switch circuit 14. Resistor 104 limits the current through transistor 102. Transistor 98 drives switching transistor 80 in the same manner as transistor 102. The emitter of transistor 88 is connected to the positive high voltage level at buffer capacitor 78 and the emitter transistor 80 is connected to the negative high voltage of buffer capacitor 74. The collectors of transistors 80 and 88 are connected together and are connected to output terminal 22 via resistor 96. Resistor 94 permits buffer capacitors 74 and 78 to slowly discharge to a lower level if set by potentiometer 28.

Although the invention has been described and illustrated with reference to a particular embodiment, it is to be appreciated and understood that various adaptations and modifications may be made without departing from the scope of the invention as set forth by the appended claims.

The invention is claimed in accordance with the following:

1. A pulse generator circuit for generating timed pulses of regulated amplitude and constant width comprising:

oscillator means for providing timing pulses;

trigger circuit means for receiving said timing pulses and for generating trigger signals of predetermined pulse width;

driver circuit means for receiving said trigger signals and for generating driving signals;

voltage conversion means for providing adjustable regulated voltages; and switching means for receiving said driving signals and said adjustable regulated voltages and producing output timed pulses of amplitude equal to said regulated voltages and of constant width.

2. A pulse generator circuit according to claim 1 wherein said trigger circuit means includes delay means and feed back means.

3. A pulse generator circuit according to claim 1 wherein said voltage conversion means comprises adjustable regulated high voltage supply means and a fixed unregulated low voltage supply means.

4. A pulse generator circuit according to claim 1 said voltage conversion means includes over voltage-limiting means.

5. A pulse generator circuit according to claim 4 wherein said over voltage-limiting means defines a feedback circuit.

6. A pulse generator circuit according to claim 4 wherein said over voltage-limiting means defines shunt regulating means.

7. A pulse generator circuit according to claim 1 further including power supply means defining rechargeable battery means for supplying a predetermined voltage and said voltage conversion means includes means for preventing discharge failure modes of said rechargeable battery means.

8. A pulse generator circuit according to claim 1 wherein said oscillator means and trigger circuit means comprise complementary metal oxide silicon (CMOS) devices.

9. A nerve stimulating device for stimulating nerves of a body comprising:

oscillator means for producing variable rate timing pulses;

trigger circuit means for receiving said timing pulses and for generating trigger signals of predetermined pulse width;

driver circuit means for receiving said trigger signals and for generating driving signals in response thereto;

voltage conversion means for providing adjustable regulated voltages; and switching means for receiving said driving signals and said adjustable regulated voltages and producting output timed pulses of amplitude equal to said regulated voltages and of constant width; and electrode means connected to said switching means and adapted to be secured to a selected area of a body so that said timed pulses stimulate the nerves at said selected area.

10. A nerve stimulating device according to claim 9 wherein said adjustable regulated voltages are of substantially equal amplitude and of opposite polarity.

11. A nerve stimulating device according to claim 9 wherein said voltage conversion means includes over voltage-limiting means for preventing the regulated voltages from exceeding a predetermined level.

12. A nerve stimulating device according to claim 9 further including power supply means defining rechargeable battery means.

* * * * *